United States Patent [19]
Sheen et al.

[11] Patent Number: 6,156,915
[45] Date of Patent: Dec. 5, 2000

[54] REACTIVE AND DURABLE ANTI-STATIC AGENT AND METHOD OF PREPARING THE SAME

[75] Inventors: Yuung-Ching Sheen, Tainan Hsien; Ling-Yu Cheng, Taipei Hsien; Juh-Shyong Lee; Tsai-Wie Tseng, both of Hsinchu, all of Taiwan

[73] Assignee: Industrial Technology Research Institute, Hsinchu, Taiwan

[21] Appl. No.: 08/878,605

[22] Filed: Jun. 19, 1997

[51] Int. Cl.⁷ .................. C07D 303/36; C07C 209/00
[52] U.S. Cl. ............... 549/551; 549/518; 564/469
[58] Field of Search .................... 549/518, 551; 564/469

*Primary Examiner*—Amelia Owens
*Attorney, Agent, or Firm*—Sughrue, Mion, Zinn, Macpeak & Seas, PLLC

[57] ABSTRACT

A reactive and durable anti-static agent and the method of preparing the anti-static agent comprises: a compound with an amine group and a compound with an epoxide group added into the flask, stirred under the gradual raised temperature, reacted into an anti-static agent with a reactive functional group under proper temperature. The characteristics of the invention is that the reaction of preparing the anti-static agent is very active, and the preparing method is easy. With the reactive functional groups and polymer additives which enable the reaction in polymer, in addition to the endurance and a long lifetime, the surface property of the anti-static agent is improved. Therefore, the anti-static prepared according to the invention is broadly in use of industry.

32 Claims, No Drawings

REACTIVE AND DURABLE ANTI-STATIC AGENT AND METHOD OF PREPARING THE SAME

BACKGROUND OF THE INVENTION

1. Field of the Invention

The invention relates in general to an anti-static agent and the preparing method of it, and more particularly to a reactive and durable anti-static agent and the preparing method of it. In the invention, a compound with an amine ($NH_2$) group and a compound with an epoxide group are reacted into a reactive and durable anti-static agent.

2. Description of the Related Art

The conventional anti-static agent is a kind of additive, and normally, is a quaternary ammonium salt with a low molecular weight or a conductive carbon black additive to improve the anti-static property. For example, in U.S. Pat. No. 5,128,473 and Japanese Patent No. 349,053, when this kind of material is in use, the quaternary ammonium salt with a low molecular weight is easily migrated and lapsed. The surface of the polymer becomes humid after a period of time, and thus, the polymer is deteriorated. With too much additive, the properties of polymer is affected, and with the carbon black additive, in addition to decarboniation, the color is restricted in a certain range, and there exists the problem of compatibility.

In another way to prepare an anti-static agent, an organic silicon compound is used as a conductive polymer mixed with a polymer, or coated on the surface of a polymer. This kind of polymer is not easily compatible with other polymers, therefore, in most cases, is formed by coating, for example, the compound disclosed in U.S. Pat. No. 4,584, 342. This kind of product is normally in additive type, with a shorter lifetime and worse wiping and water sustainability compared to a reactive anti-static agent.

In U.S. Pat. Nos. 5,356,959, and 4,931,506, and Japanese No. 5,262,460, and 5,051,475, a polyethylene oxide (PEO) is added into the polymer. Though the polyethylene oxide is with a hydroxy (OH) group which is a reactive functional group, due to its long reacting time, it has to be reacted in a high temperature which decomposes the polymer.

SUMMARY OF THE INVENTION

It is therefore an object of the invention to provide an anti-static agent and the preparing method of it to improve the properties in the conventional material.

According to the object of the invention, a kind of anti-static agent is provided and its molecular structure is shown as (I) and (II) below.

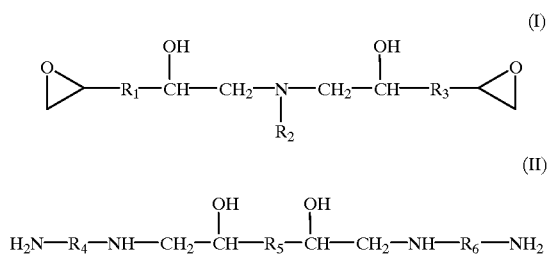

Compound (I) is an anti-static agent with an epoxide group, and compound (II) is an anti-static agent with an amine group. Since both epoxide group and amine group are reactive functional groups, compound (I) and compound (II) are reactive to enable reaction in the polymer. Therefore, the anti-static agent in the invention has the reactive property and a long lifetime.

In compound (I) and (II), the molecular weights of the alkylene oxide chains, $R_2$ group, $R_4$ group, and $R_6$ group are about 550 g/mole to 2020 g/mole; and the molecular weights of the aromatic hydrocarbon chains or the hydrocarbon chains, or the aromatic hydrocarbon chains or the hydrocarbon chains with a halogen group, $R_1$ group, $R_3$ group, and $R_5$ group are about 44 g/mole to 20000 g/mole. The structure of the alkylene group is $-(R_0-O)_n$ in which $R_0$ group is a hydrocarbon group with 2 or 3 carbon atom, and n is about 10 to 45.

According to the invention, a preparing method of an anti-static comprises: a compound with an amine group and a compound with an epoxide group added into the reacting chamber with a equivalence ½ to 2; stirred under gradual raised temperature in the range of about 30° C. to 180° C., and the compound with an amine group and the compound with an epoxide group reacted into an anti-static agent with an reactive group. The reaction can be added with catalyzers such as oxybenzene, aceticacid, alcohol, nitrobenzene, dioxane, methylbenzene, and di-I-propyl ether to speed up the reaction. In the molecular structure of the anti-static agent in the invention, the epoxide group and the amine group are reactive functional groups, in which the alkylene oxide chain provides the anti-static property.

The structure of the compound with amine group to prepare an anti-static agent is $H_2N-R_7$ or $H_2N-R_8-NH_2$, in which $R_7$ group, $R_8$ group includes alkylene oxide group. The molecular weight of the compound is about 550 g/mole to 2020 g/mole, and the structure of the alkylene is $-(R_0-O)_n$ in which $R_0$ group is a hydrocarbon group with 2 or 3 carbon atoms, and n is about 10 to 45.

The structure of the compound with an epoxide group is

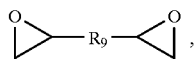

in which $R_9$ group is an aromatic hydrocarbon chain or a hydrocarbon chain, or an aromatic hydrocarbon chain or a hydrocarbon chain with halogen group with a molecular weight of about 44 g/mole to 2000 g/mole.

One of the characteristics of the invention is that the reaction of the compound with an amine group and an epoxide group are very active, and the preparing method is very easy. Thus, it can be broadly applied in industry, such as the preparing of resin, plastic, special chemistry, painting, and electronic communication products. The anti-static agent in the invention is a product with a high added value.

Another characteristic of the invention is that the anti-static agent is in a reactive type. Thus, the disadvantage in quaternary ammonium salt with a low molecular weight is eliminated. Also, with the carbon black additive, decarbonation, restriction of colors, and the compatibility with polymer are all improved.

The other characteristic of the invention is that due to the reactive functional group of the anti-static agent, the anti-static agent has a long lifetime and endurance, and the surface properties is improved.

DESCRIPTION OF THE PREFERRED EMBODIMENT

Embodiment 1

To achieve the object of the invention, an example is provided to prepare an anti-static agent in this embodiment.

A flask in which there is a stirrer, a reflux condenser, an inlet for adding material, and another inlet for nitrogen is provided. With about 152 g of the compound with an epoxide group, BE-188, having the formula:

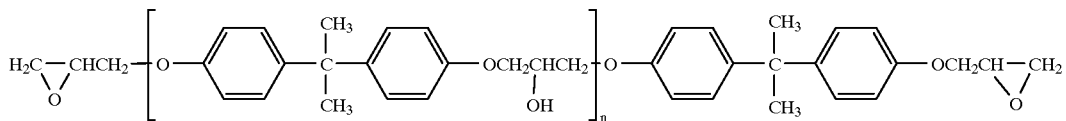

n = 0.0–0.2 made by Chang Chun Co., and with about 200 g of the compound with an amine group, M-1000 having the formula

made by Huntsman Co. added into the flask, at about 30° C. to 70° C., the anti-static agent with an epoxide group is obtained after reaction time of one hour. In BE-188 the average molecular weight is 380 g/mole, and the equivalence of the epoxide group is about 185 to 195. In M-1000, the average molecular weight is about 1000 g/mole, and the equivalence of the amine group is about 500.

Embodiment 2

To achieve the object of the invention, another example is provided to prepare an anti-static agent in this embodiment. A flask in which there is a stirrer, a reflux condenser, an inlet for adding material, and another inlet for nitrogen is provided. With about 76 g of the compound with an epoxide group, BE-188, made by Chang Chun Co., and with about 200 g of the compound with an amine group, M-2070, having the formula

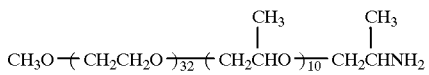

made by Huntsman Co. added into the flask, at about 50° C. to 80° C., the anti-static agent with an epoxide group is obtained after reaction time of one hour. In M-2070, the average molecular weight is about 2000 g/mole, and the equivalence of the amine group is about 1000.

Embodiment 3

To achieve the object of the invention, another example is provided to prepare an anti-static agent in this embodiment. A flask in which there is a stirrer, a reflux condenser, an inlet for adding material, and another inlet for nitrogen is provided. With about 131 g of the compound with an epoxide group, TBBADE (Tetra-bromo Bisphenol A Diglycidyl ether), and with about 200 g of the compound with an amine group, M-2070, made by Huntsman Co. added into the flask, at about 30° C. to 80° C., the anti-static agent with an epoxide group is obtained after reaction time of one hour. In TBBADE, the average molecular weight is about 656 g/mole, and the equivalence of the epoxide group is about 328.

Embodiment 4

To achieve the object of the invention, another example is provided to prepare an anti-static agent in this embodiment. A flask in which there is a stirrer, a reflux condenser, an inlet for adding material, and another inlet for nitrogen is provided. With about 190 g of the compound with an epoxide group, Epikote 1007, having the formula

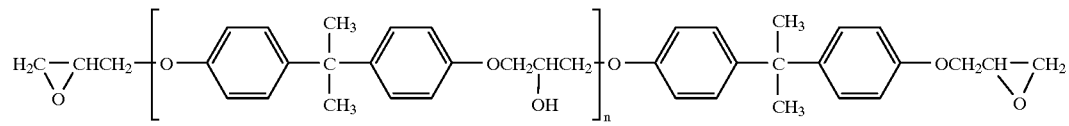

n = 10.5–12.5 made by Shell Co., and with about 25 g of the compound with an amine group, M-1000, made by Huntsman Co. added into the flask, at about 60° C. to 150° C., the anti-static agent with an epoxide group is obtained after reaction time of one hour. In Epikote 1007, the average molecular weight is about 2900 g/mole, and the equivalence of the epoxide group is about 1750 to 2100.

Embodiment 5

To achieve the object of the invention, another example is provided to prepare an anti-static agent in this embodiment. A flask in which there is a stirrer, a reflux condenser, an inlet for adding material, and another inlet for nitrogen is provided. With about 193 g of the compound with an epoxide group, Epikote 1007, made by Shell Co., and with about 50 g of the compound with an amine group, M-2070, made by Huntsman added into the flask, at about 60° C. to 150° C., the anti-static agent with an epoxide is obtained after reaction time of one hour.

Embodiment 6

To achieve the object of the invention, another example is provided to prepare an anti-static agent in this embodiment. A flask in which there is a stirrer, a reflux condenser, an inlet for adding material, and an inlet for nitrogen is provided. With about 80 g of the compound with an epoxide group, BDDE (Butane Diol Diglycide Ether), and with about 200 g of the compound with an amine group, M-1000, made by Huntsman added into the flask, at about 50° C. to 100° C., the anti-static agent with an epoxide is obtained after reaction time of one hour. In BDDE, the average molecular weight is about 202 g/mole, and the equivalence of the epoxide group is about 100.

Embodiment 7

To achieve the object of the invention, another example is provided to prepare an anti-static agent in this embodiment.

A flask in which there is a stirrer, a reflux condenser, an inlet for adding material, and another inlet for nitrogen is provided. With about 26 g of the compound with an epoxide group, DGE (Diglycide Ether), and with about 200 g of the compound with an amine group, M-2070, made by Huntsman added into the flask, at about 30° C. to 70° C., the anti-static agent with an epoxide is obtained after reaction time of thirty minutes. In DEG, the average molecular weight is about 130 g/mole, and the equivalence of the epoxide group is about 65.

Embodiment 8

To achieve the object of the invention, another example is provided to prepare an anti-static agent in this embodiment. A flask in which there is a stirrer, a reflux condenser, an inlet for adding material, and another inlet for nitrogen is provided. With about 19 g of the compound with an epoxide group, BE-188, made by Chang Chun Co., and with about 200 g of the compound with an amine group, M-2070, made by Huntsman added into the flask, at about 30° C. to 70° C., the anti-static agent with an epoxide is obtained after reaction time of one hour. In ED-2001, having the formula

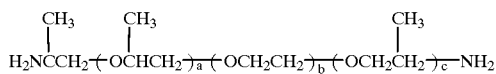

the average molecular weight is about 2002 g/mole, and the equivalence of the amine group is about 1000.

Embodiment 9

Table 1 shows that in embodiment 4 according to the invention, a comparison of anti-static properties for the reaction products by the ratios of the anti-static agent versus different cross-linking agents. Referring to Table 1, by performing the experiment mentioned in embodiment 4 three times, the obtained anti-static agent with epoxide group is added with cross linking agents, such as an MEA (Monoethanol Amine) and an ED2001 and an EDR-148, having the formula

made by Huntsman Co., respectively. Then, by cross linking reaction for about one hour at 50° C. to 80° C., an anti-static epoxy resin is obtained. Furthermore, from the surface resistance date shown in Table 1, it is known that the anti-static property of the anti-static agent is very effective.

TABLE 1

|  | Weight Percentage (%) | Weight Percentage (%) | Weight Percentage (%) |
|---|---|---|---|
| The Anti-Static Agent obtained in Embodiment 4 | 88 | 54 | 72.9 |
| MEA | 12 | 0 | 0 |
| ED2001 | 0 | 42.7 | 27.1 |
| EDR148 | 0 | 3.3 | 0 |
| Surface Resistance of Product ($\Omega$/ ) | $10^{10.5}$ | $10^{8.2}$ | $10^{9.5}$ |

One of the characteristics of the invention is that the reaction of the compound with an amine group and an epoxide group is very active, and the preparing method is easy. Thus, it can be broadly applied in industry, such as the preparing of resin, plastic, special chemistry, painting, and electronic communication products. The anti-static agent in the invention is a product with a high added value.

Another characteristic of the invention is that the anti-static agent is in a reactive type. Thus, the disadvantage in quaternary ammonium salt with a low molecular weight is eliminated. Also, with the carbon black additive, decarbonation, restriction of colors, and the compatibility with polymer are all improved.

The other characteristic of the invention is that due to the reactive functional group of the anti-static agent, the anti-static agent has a long lifetime and endurance, and the surface properties is improved as well.

While the invention has been described by way of example and terms of a preferred embodiment, it is to be understood that the invention is not limited thereto. To the contrary, it is intended to cover various modifications and similar arrangements and procedures, and the scope of the appended claims therefore should be accorded the broadest interpretation so as to encompass all such modifications and similar arrangements and procedures.

What is claimed is:

1. A reactive and durable anti-static agent, the structure of the anti-static agent comprising:

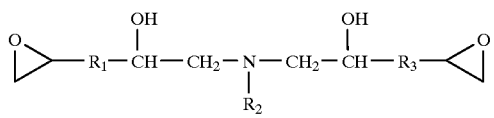

wherein $R_2$ is an alkylene oxide group, and $R_1$ and $R_3$ each is a hydrocarbon group.

2. An anti-static agent according to claim 1, wherein the structure of the alkylene oxide group is $-(R_0-O)_n-$, wherein $R_0$ is a hydrocarbon group with 2 or 3 carbon atoms, and n is about 10 to 45.

3. An anti-static agent according to claim 1, wherein the molecular weight of $R_2$ is about 550 g/mole to 2020 g/mole.

4. An anti-static agent according to claim 1, wherein the molecular weight of $R_1$ is about 44 g/mole to 2000 g/mole.

5. An anti-static agent according to claim 1, wherein the hydrocarbon group is an aromatic hydrocarbon group.

6. An anti-static agent according to claim 1, wherein the hydrocarbon group is an aliphatic hydrocarbon group.

7. An anti-static agent according to claim 1, wherein the hydrocarbon group is an aromatic hydrocarbon group with a halogen atom.

8. An anti-static agent according to claim 1, wherein the hydrocarbon group is an aliphatic hydrocarbon group with a halogen atom.

9. A reactive and durable anti-static agent, the structure of the anti-static agent comprising:

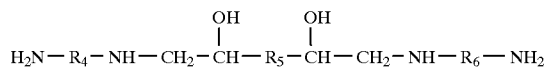

wherein $R_4$ and $R_6$ each is an alkylene oxide group, and $R_5$ is a hydrocarbon group.

10. An anti-static agent according to claim 9, wherein the structure of the alkylene oxide group is $-(R_0-O)_n-$, wherein $R_0$ is a hydrocarbon group with 2 or 3 carbon atoms, and n is about 10 to 45.

11. An anti-static agent according to claim 9, wherein the molecular weight of the $R_2$ is about 550 g/mole to 2020 g/mole.

12. An anti-static agent according to claim 9, wherein the molecular weight of $R_1$ group is about 44 g/mole to 2000 g/mole.

13. An anti-static agent according to claim 9, wherein the hydrocarbon group is an aromatic hydrocarbon group.

14. An anti-static agent according to claim 9, wherein the hydrocarbon group is an aliphatic hydrocarbon group.

15. An anti-static agent according to claim 9, wherein the hydrocarbon group is an aromatic hydrocarbon group with a halogen atom.

16. An anti-static agent according to claim 9, wherein the hydrocarbon group is a aliphatic hydrocarbon group with a halogen atom.

17. A method of preparing a reactive and durable anti-static agent comprising: reacting a first compound with an amine group and a second compound with an epoxide group at a certain ratio and at a certain temperature to form the reactive and durable anti-static agent.

18. A method according to claim 17, wherein a structure of the first compound with the amine group is:

wherein $R_7$ contains an alkylene oxide group.

19. A method according to claim 18, wherein the molecular weight of the alkylene oxide group is about 550 g/mole to 2020 g/mole.

20. A method according to claim 18, wherein the structure of the alkylene oxide group is $-(R_0-O)_n-$, wherein $R_0$ is a hydrocarbon group with 2 or 3 carbon atoms, and n is about 10 to 45.

21. A method according to claim 17, wherein the structure of the first compound with the amine group is:

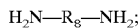

wherein $R_8$ group is an alkylene oxide group.

22. A method according to claim 21, wherein the molecular weight of the alkylene oxide group is about 550 g/mole to 2020 g/mole.

23. A method according to claim 21, wherein the structure of the alkylene oxide group is $-(R_0-O)_n-$, wherein $R_0$ is a hydrocarbon group with 2 or 3 carbon atoms, and n is about 10 to 45.

24. A method according to claim 17, wherein the structure of second compound with the epoxide group is:

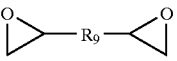

wherein the $R_9$ is a hydrocarbon group.

25. A method according to claim 24, wherein the molecular weight of $R_1$ is about 44 g/mole to 2000 g/mole.

26. A method according to claim 24, wherein the hydrocarbon group is an aromatic hydrocarbon group.

27. A method according to claim 24, wherein the hydrocarbon group is an aliphatic hydrocarbon group.

28. A method according to claim 24, wherein the hydrocarbon group is an aromatic hydrocarbon group with a halogen.

29. A method according to claim 24, wherein the hydrocarbon group is an aliphatic hydrocarbon group with a halogen atom.

30. A method according to claim 17, wherein the equivalence ratio of the first compound with the amine group to the second compound with the epoxide group is about ½ to 2.

31. A method according to claim 17, wherein the temperature is about 30° C. to 200° C.

32. A method according to claim 31, wherein the temperature is about 60° C. to 120° C.

* * * * *